United States Patent
Fellner et al.

(10) Patent No.: US 12,000,587 B2
(45) Date of Patent: Jun. 4, 2024

(54) METHOD FOR ANALYZING AND OPTIMIZING THE OPERATION OF WASTE INCINERATOR SYSTEMS

(71) Applicant: TECHNISCHE UNIVERSITÄT WIEN, Vienna (AT)

(72) Inventors: Johann Fellner, Vienna (AT); Therese Schwarzböck, Vienna (AT)

(73) Assignee: TECHNISCHE UNIVERSITÄT WIEN, Vienna (AT)

( * ) Notice: Subject to any disclaimer, the term of this patent is extended or adjusted under 35 U.S.C. 154(b) by 306 days.

(21) Appl. No.: 17/620,272

(22) PCT Filed: Jun. 17, 2020

(86) PCT No.: PCT/AT2020/060246
§ 371 (c)(1),
(2) Date: Dec. 17, 2021

(87) PCT Pub. No.: WO2020/252513
PCT Pub. Date: Dec. 24, 2020

(65) Prior Publication Data
US 2022/0373174 A1    Nov. 24, 2022

(30) Foreign Application Priority Data

Jun. 21, 2019    (AT) ................ A50555/2019

(51) Int. Cl.
*F23G 5/50* (2006.01)
*F23N 5/00* (2006.01)
*G16C 20/10* (2019.01)

(52) U.S. Cl.
CPC ............. *F23G 5/50* (2013.01); *F23N 5/003* (2013.01); *G16C 20/10* (2019.02); *F23G 2207/20* (2013.01); *F23N 2900/05002* (2013.01)

(58) Field of Classification Search
CPC ........................................................ F23G 5/50
(Continued)

(56) References Cited

U.S. PATENT DOCUMENTS

| | | | |
|---|---|---|---|
| 4,984,524 | A | 1/1991 | Mindermann |
| 7,832,342 | B2 | 11/2010 | Martin |

FOREIGN PATENT DOCUMENTS

| | | |
|---|---|---|
| EP | 0317731 A1 | 5/1989 |
| EP | 1698827 A2 | 9/2006 |
| EP | 1715339 A2 | 10/2006 |

OTHER PUBLICATIONS

Mohn, S. Szidat, J. Fellner, H. Rechberger, R. Quartier, B. Buchmann, L. Emmenegger. Determination of biogenic and fossil CO2 emitted by waste incineration based on 14CO2 and mass balances, Bioresource Technology, vol. 99, Issue 14, 2008.*

(Continued)

*Primary Examiner* — Vivek K Shirsat
(74) *Attorney, Agent, or Firm* — LUCAS & MERCANTI, LLP; Klaus P. Stoffel

(57) ABSTRACT

A method for analyzing or optimizing the operation of waste incinerator systems. The content of CO2 is measured in the exhaust gas and is used to determine the ratio of biogenic carbon to fossil carbon in the incinerated waste, if necessary after resetting to the CO2 reference quantity. The variability of the CO2 reference or the ratio of biogenic carbon to fossil carbon in the incinerated waste is determined and recorded according to quantity and duration. When optimizing the operation, the location of the waste in the bunker, from which the incinerated waste originates with a composition or variability that has now been ascertained using the method, is used to further remove or mix the waste.

6 Claims, 9 Drawing Sheets

(58) Field of Classification Search
USPC .............................. 431/12, 5; 110/235, 236
See application file for complete search history.

(56) References Cited

OTHER PUBLICATIONS

International Search Report Dated Oct. 5, 2020, PCT/AT2020/060246, 2 Pages.

* cited by examiner

METHOD FOR ANALYZING AND OPTIMIZING THE OPERATION OF WASTE INCINERATOR SYSTEMS

CROSS-REFERENCE TO RELATED APPLICATIONS

The present application is a 371 of International application PCT/AT2020/060246, filed Jun. 17, 2020, which claims priority of AT A50555/2019, filed Jun. 21, 2019, the priority of these applications is hereby claimed and these applications are incorporated herein by reference.

BACKGROUND OF THE INVENTION

The invention relates to a method for analyzing the operation and for optimizing the operation of garbage incineration plants.

From EP 1 698 827 it is known practice to determine the $CO_2$ content of the flue gas from, for example, a garbage incineration plant in order on that basis to gauge the "combustion intensity" and, if a certain level is exceeded, to regulate the ratio of the oxygen mass flow rates of primary combustion gas and secondary combustion gas in such a way that it drops below this level again.

From the applicant's EP 1 715 339 it is known practice, for the purpose of ascertaining the fractions of biogenic and fossil energy sources of a garbage incineration plant, to perform mandatory equalization of at least three balances selected from eight balances. This method is very exact, but requires a certain cost and complexity of apparatus and process.

Garbage incineration plants, as the name indeed suggests, carry out incineration of garbage and hence of a fuel which has a very heterogeneous composition and more particularly a fluctuating ratio of biogenic waste constituents to fossil waste constituents, including plastics of all kinds, among others. Every garbage incineration plant is designed for a ratio between these two fractions that is anticipated on the basis of studies, and exhibits the best operating results when that ratio is present. As a result of the entirely erratic supply of waste—this is the case even when extremely uniform mixing is the aim when charging the bunker and when circulating the waste in the bunker from which the combustion chamber of the garbage incineration plant receives its combustion material, on the basis of empirical values—there are, over time, unwanted changes in the fuel composition in the combustion chamber, which affects the incineration process, the energy recovered (converted), and the flue gas properties as well, where these changes can best be made manifest.

The following must also be noted: there is not really a precisely defined ratio of biogenic to fossil carbon as a design parameter for garbage incineration plants. Nor is it a problem, in terms of technical operation, to operate the plant with a constant different ratio of biogenic to fossil. What is problematic are short-term changes in the composition of the fuel.

Hence for virtually all kinds of fossil fuels, based on stoichiometric supply of air (hence 0 vol % of oxygen in the flue gas), the $CO_2$ fraction obtained is between 15 and 17.6 vol % if natural gas and methane—which, indeed, occur hardly at all in garbage incineration (with the exception of supporting fuels)—are disregarded. In comparison to this, in the case of typical biogenic fuels, the $CO_2$ fraction obtained in the flue gas (with stoichiometric supply of air) is between 19.1 (kitchen wastes) and 21 (cellulose) vol %, as evident from Table 1 below.

Differences in waste composition, and the temporal fluctuations arising as a result of the random supply, are inconvenient since garbage incineration plants are typically also used for energy recovery (in actual fact, conversion) and for that purpose the amount of steam (at constant temperature and constant pressure) generated per hour is to be as uniform as possible. In the prior art this is achieved in some cases via automated or manually controlled mixing of the supplied waste in the garbage bunker, using the bunker crane (see FIG. 3—left-hand diagram), and in extreme cases by supply of fuel oil or natural gas in order to maintain sufficient energy conversion, or by acceptance of losses due to partial capacity utilization of the plant.

From existing measurements and studies on different plants, it is apparent that for a garbage incineration plant having an annual capacity of 200 000 metric tons, as a result in particular of short-term fluctuations in the composition of the fuel supply, between €200 000.00 and €500 000.00 cannot be earned or must be spent on ancillary fuels (typically natural gas or fuel oil), which not only represents a large sum per plant but also becomes a significant economic quantity, owing to the fact that in Europe there are about 400 garbage incineration plants with a size of this kind.

SUMMARY OF THE INVENTION

It is an aim and object of the invention to specify a method of the above-stated kind that allows the variations in operation to be reduced.

This is accomplished, in accordance with the invention, by a method in which the composition of the flue gas is monitored continually at least for the $CO_2$ content and, from the result of the measurement, the need for a change in the composition of the fuel supply (that is, better mixing) is derived and implemented. In one embodiment, this parameter is used to gauge the composition of the waste in the bunker, and the change in the charging or mixing of the fuel is implemented with regard to this composition.

BRIEF DESCRIPTION OF THE DRAWING

The invention is described in more detail below with reference to the drawing, in which.

DETAILED DESCRIPTION OF THE INVENTION

Figure 1:
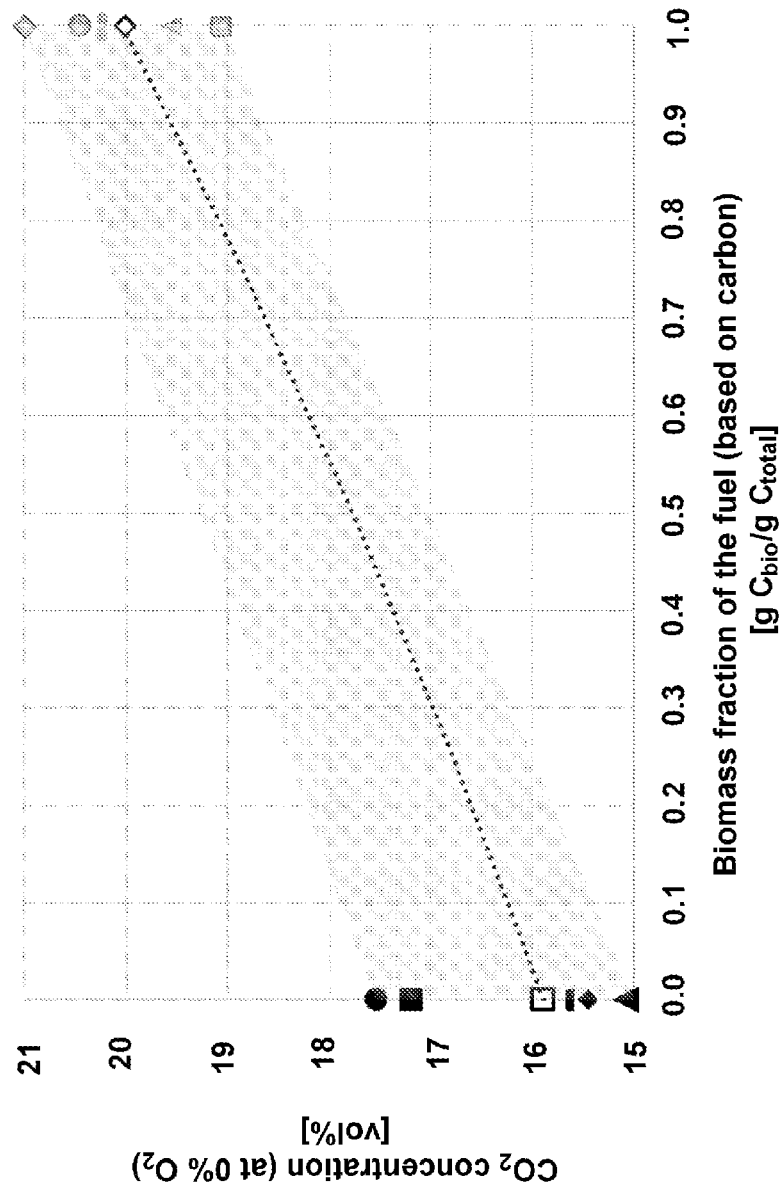
FIG. 1 shows the association between the flue gas composition and the fuel composition in respect of biogenic/fossil material.

Before addressing the individual representations in the drawing in more detail, the theoretical basis of the invention will be set out:

The combustion of different fuels is associated with a respectively characteristic flue gas composition (amount of $O_2$ and $CO_2$ in the dry flue gas—this can be obtained by calculating back from the amount measured in the damp flue gas, but in contrast to that amount is directly comparable and meaningful), this composition being dependent not only on the chemical composition of the fuel (amount of water, C, H, O, N, S, F, Cl, etc.) but also on the amount of the combustion air. For example, a larger amount of combustion air in the case of a particular fuel results in a higher $O_2$ concentration and a lower $CO_2$ concentration in the flue gas.

Through an arithmetic normalization of the flue gas composition to a constant oxygen content in the flue gas (e.g., residual oxygen content of 0% for stoichiometric air demand or constant air ratio number), changes in the flue gas composition are dependent exclusively on the fuel or its chemical composition.

This normalization of the flue gas composition (to an arbitrary flue gas oxygen content $O_{2_{reference}}$) takes place by means of the following equation, which is common knowledge, and which allows an approximate calculation of the dry flue gas composition for a constant oxygen content in the flue gas.

$$CO_{2_{reference}} = \frac{CO_{2_{measured}} \cdot (21 - O_{2_{reference}})}{(21 - O_{2_{measured}})}$$

$CO_{2_{reference}}$  $CO_2$ concentration in the dry flue gas at constant air ratio number (to be set arbitrarily) or at $CO_{2_{reference}}$ [vol %]

$CO_{2_{measured}}$ measured $CO_2$ concentration in the dry flue gas of the incineration plant [vol %]

$CO_{2_{measured}}$ measured $O_2$ concentration in the dry flue gas of the incineration plant [vol %]

$O_{2_{reference}}$ (constant) oxygen content, to be set arbitrary, in the dry offgas of the incineration plant (preferably a value of 0 vol % is chosen) [vol %]

21 stands for $O_{2_{atm}}$, the atmospheric oxygen content [vol %]

For an exact calculation (taking account of the existing $CO_2$ content in the combustion air/in the atmosphere) of the normalized $CO_2$ concentration $CO_{2_{reference}}$ in the dry flue gas at constant air ratio number (to be set arbitrarily) or for $O_{2_{reference}}$, the formula below is to be used; significant differences between the results of the approximation formula and of the exact formula occur only at relatively air ratio numbers.

$$CO_{2_{reference}} = \left(CO_{2_{measured}} - \frac{CO_{2_{atm}} \cdot (100\% - CO_{2_{measured}} - O_{2_{measured}})}{(100\% - O_{2_{atm}} - CO_{2_{atm}})}\right) \cdot$$

$$\frac{(O_{2_{atm}} - O_{2_{reference}})}{(O_{2_{atm}} - O_{2_{measured}})} + CO_{2_{atm}} \cdots$$

$$\left(100\% - \left(CO_{2_{measured}} - \frac{CO_{2_{atm}} \cdot (100\% - CO_{2_{measured}} - O_{2_{measured}})}{(100\% - O_{2_{atm}} - CO_{2_{atm}})}\right)\right.$$

$$\left.\cdots \frac{(O_{2_{atm}} - O_{2_{reference}})}{(O_{2_{atm}} - O_{2_{measured}})}\right)$$

$O_{2_{atm}}$  $O_2$ concentration in the incineration air/in the atmosphere [vol %]; typically this is around 20.94 vol %

$CO_{2_{atm}}$  $CO_2$ concentration in the incineration air/in the atmosphere [vol %]; typically this is around 0.04 vol %

As already mentioned above, the dry flue gas composition normalized to a constant flue gas oxygen content, $CO_{2_{reference}}$ and $O_{2_{reference}}$, is dependent exclusively on the fuel or its chemical composition.

Accordingly, temporal variations in the dry flue gas composition (amount of $CO_{2_{reference}}$) referred (normalized) to a constant oxygen content $O_{2_{reference}}$ are the result of a fuel with a (temporally) changed composition.

Accordingly, for garbage incineration plants, the homogeneity/mixing of the garbage input can be gauged from the temporal variation of $CO_{2_{reference}}$. A virtually constant value of $CO_{2_{reference}}$ suggests effective mixing and constant composition of the waste input, whereas (short-term) changes in $CO_{2_{reference}}$ point to a fluctuating waste composition (and therefore inadequate mixing).

Bunker garbage mixing can be monitored and hence also controlled on the basis of the temporal variation of $CO_{2_{reference}}$.

The aim of the garbage incineration plant operator is to ensure maximally constant (small fluctuations) composition of the waste input, since this is the only way of ensuring optimal (energy-efficient) operation.

Table 1 below, already addressed above, shows examples of normalized flue gas composition (flue gas composition referred to 0 vol % oxygen) for different fuels, expressed by $CO_{2_{reference}}$.

TABLE 1

| Fuel/waste | $O_{2_{reference}}$ [vol %] | $CO_{2_{reference}}$ [vol %] |
|---|---|---|
| Fossil fuels/wastes | | |
| Natural gas | 0 | 12 |
| Methane | 0 | 11.8 |
| Polyethylene | 0 | 15.1 |
| Polypropylene | 0 | 15.1 |
| PVC | 0 | 17.2 |
| Polystyrene | 0 | 17.6 |
| Fuel oil EL | 0 | 15.6 |
| Biogenic fuels/wastes | | |
| Cellulose | 0 | 21 |
| Wood | 0 | 20.5 |
| Paper & card | 0 | 20.1 |
| Garden wastes | 0 | 19.6 |
| Kitchen wastes | 0 | 19.1 |

From Table 1 above it is evident that in comparison to fossil fuels, biogenic fuels/wastes have a higher value of $CO_{2_{reference}}$. In simplified terms, accordingly, the normalized flue gas composition (expressed by $CO_{2_{reference}}$) can also be used to gauge the fraction of biogenic or fossil materials in the input of garbage incineration plants.

Utilization of the invention for evaluating plant operation with regard to garbage mixing: By means of the method of the invention it is not only possible to monitor, and on that basis control, the current mixing/homogenization of the bunker garbage (see FIGS. 2 and 3); instead, the method is also suitable for retrospective analysis of plant operation (with regard to the mixing/homogenization of the bunker garbage) and for quantification of the influence of inadequate mixing/homogenization of the waste on operation.

Figure 4A:
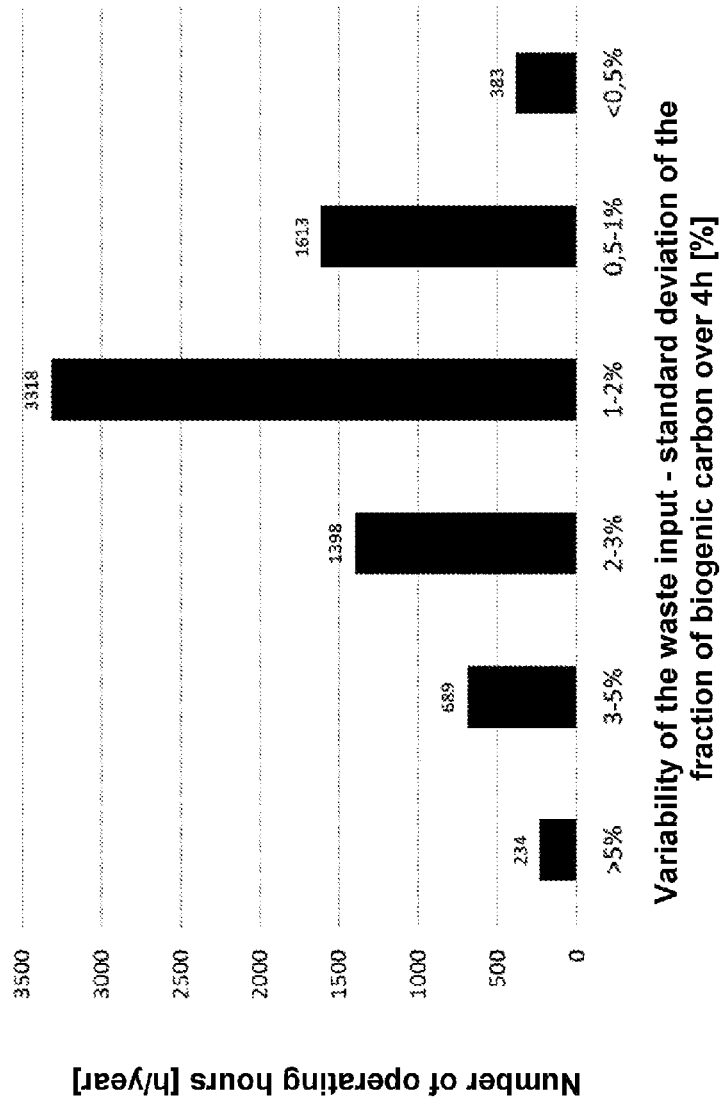
FIG. 4a and FIG. 4b show an analysis of the variability of the fuel composition of two garbage incineration plants.
Figure 4B:
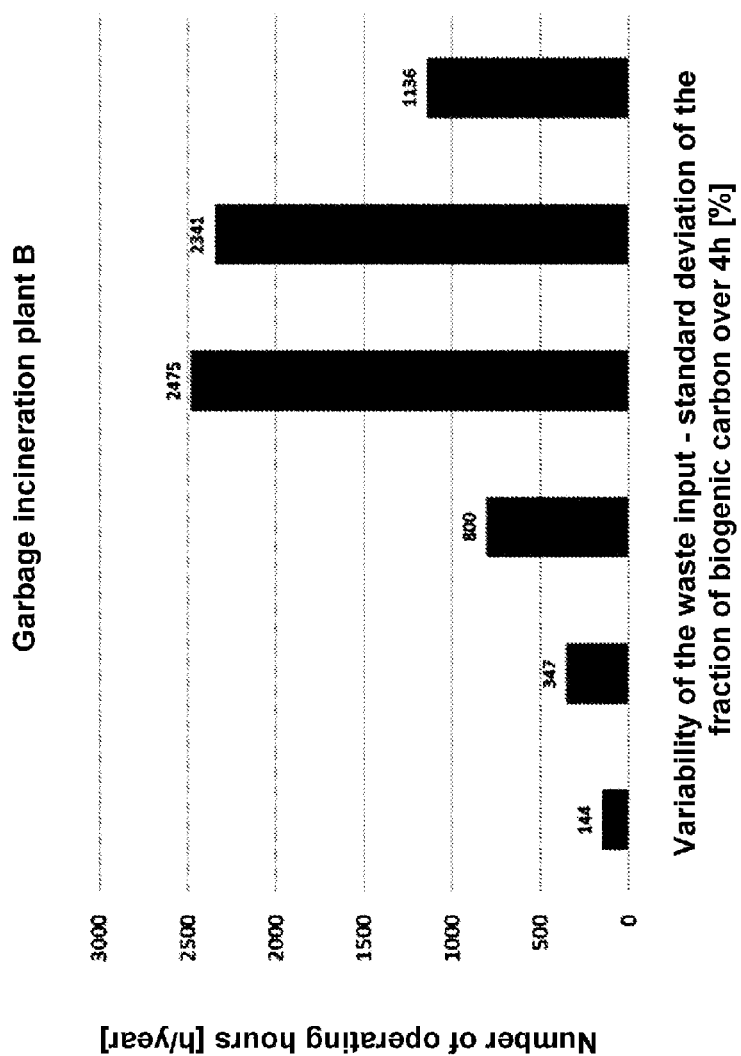

It is possible, for example, to work out the fraction of operating hours where mixing/homogenization of the bunker is very good or bad (see FIG. 4). Through statistical evaluation (e.g., averaging) of operationally relevant parameters of the garbage incineration plant (e.g. steam production, waste throughput, flue gas oxygen content, ancillary fuel consumption) for the different periods (operating hours with very good, good . . . bad mixing/homogenization of the bunker garbage), conclusions can then be drawn regarding the influence of bunker garbage mixing on operation (see FIGS. 5 and 6). This provides the plant operator with valuable information concerning the possible potential for optimization of their plant through better mixing/homogenization of the bunker garbage.

From the analyses for 2 garbage incineration plants (plants A and B) it is evident, for example, that the homogenization of the bunker garbage is achieved more effectively in plant B, as the number of operating hours with low waste input variability (expressed by the standard deviation of the fraction of biogenic carbon over 4 h) is significantly higher (see FIG. 4).

Figure 5A:
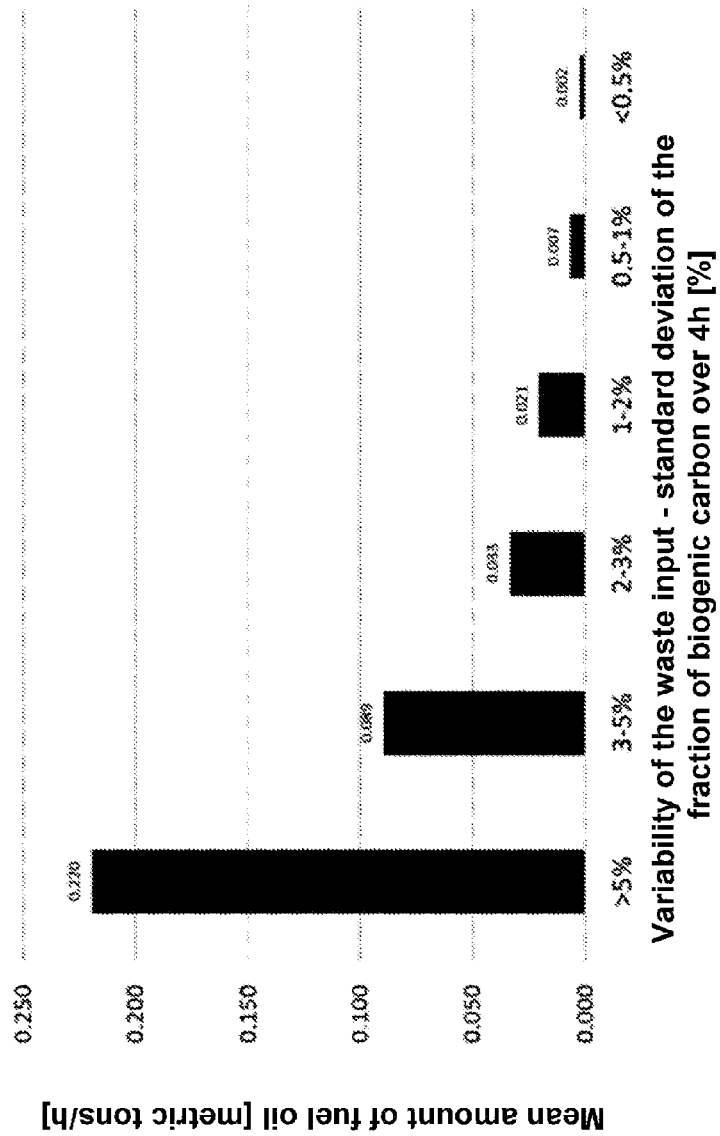
FIG. 5a and FIG. 5b show the mean consumption of ancillary fuel (using fuel oil as an example) and the mean production of steam by a garbage incineration plant, in each case as a function of the variability of the fuel composition.
Figure 5B:
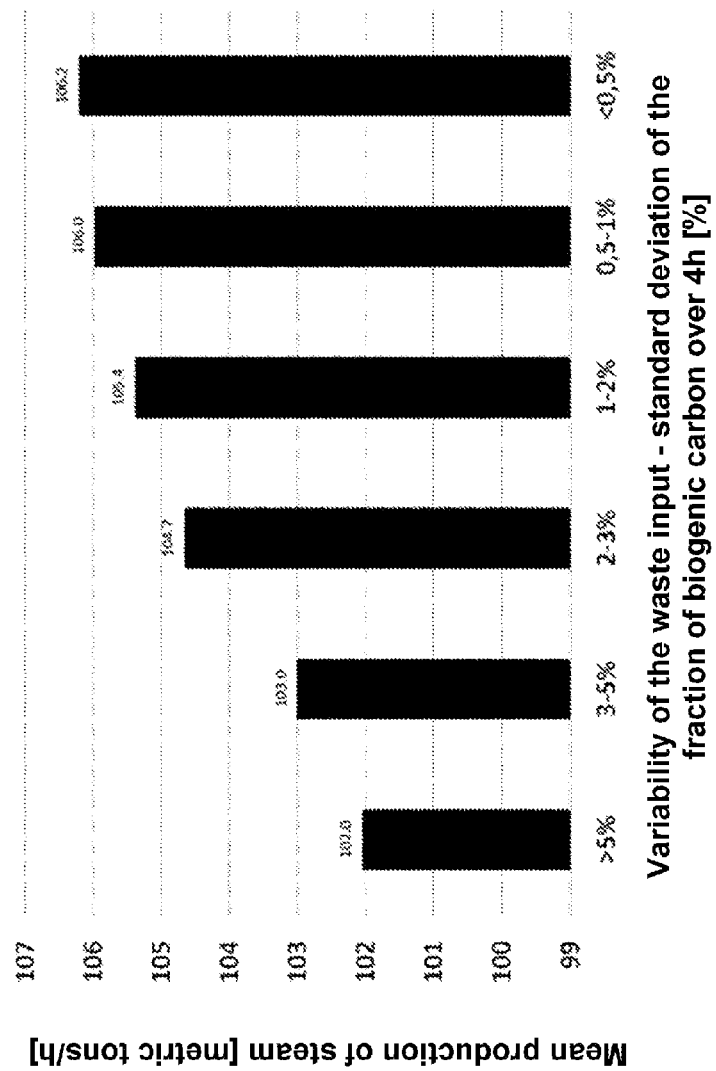
Figure 6A:
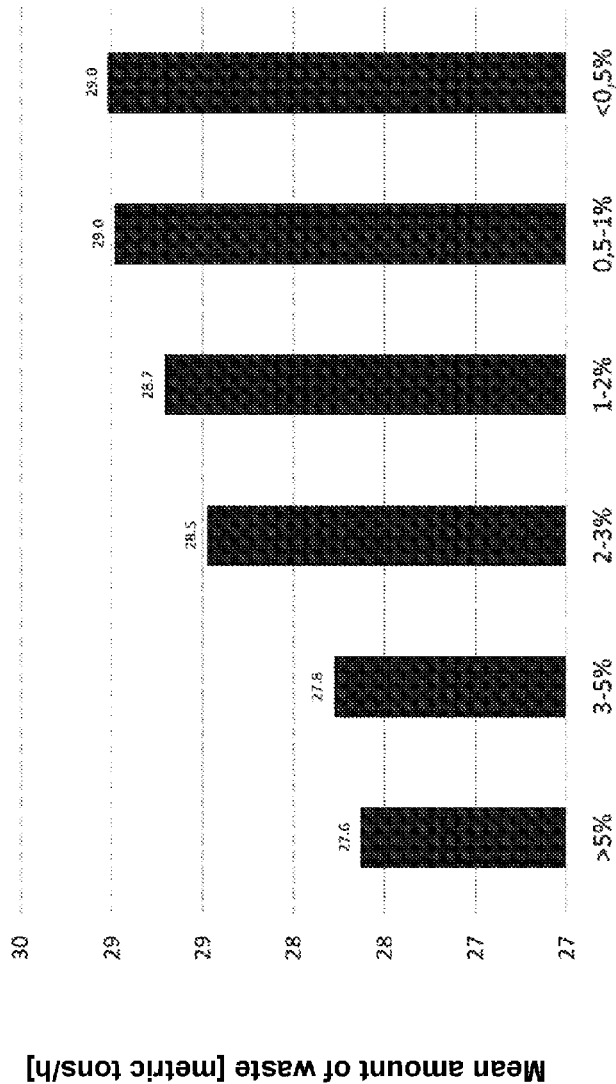
FIG. 6a and FIG. 6b show the mean waste throughput and the mean $O_2$ concentration in the flue gas of a garbage incineration plant, in each case as a function of the variability of the fuel composition.

From the evaluations relating to the influence of the temporal variability of bunker garbage composition (expressed through the standard deviation of the fraction of biogenic carbon over 4 h) on plant operation, it emerges for garbage incineration plant A that as the temporal variability of the waste composition becomes higher (standard deviation of >5% of the biogenic carbon fraction: low level of mixing/homogenization of the bunker garbage), the mean consumption of fuel increases (from approximately 0 to 225 kg/h), the mean production of steam by the plant decreases (from 106.2 t/h to 102 t/h), the mean throughput of waste decreases (from 29 t/h to 27.6 t/h), and at the same time the mean oxygen concentration in the flue gas increases (from 7.5 vol % to 8.05 vol %); see FIGS. 5 and 6. All of the effects observed lead to financial losses for the plant operator.

By means of the method of the invention, these losses can for the first time be quantified and explained in concrete terms with the temporal variability of the composition of the waste input (mixing/homogenization of the bunker garbage), and virtually in real time as well, something which was hitherto not possible.

Utilization of the invention for showing biogenic and fossil energy source fractions and fossil and biogenic carbon dioxide emissions of the incineration plant:

The method of the invention is not only suitable for optimizing operation but instead can also be used approximately for showing biogenic and fossil energy source fractions and fossil and biogenic carbon dioxide emissions of the incineration plant, using, for example, the relationship represented in FIG. 1.

FIG. 1 shows, in the form of a dotted line and, taking account of possible deviations, as grey strips, the flue gas composition (expressed in the form of the $CO_{2_{reference}}$ concentration at stoichiometric air demand) against the biomass fraction of the incinerated waste (based on carbon in g $C_{bio}$/g $C_{total}$); in a mixture with different fossil fuels. The relevant indications are as follows:

At the left-hand edge, from top to bottom, a number of fossil fuels in BLACK:
Circle: polystyrene,
Square: polyvinyl chloride,
Bordered square: typical mix of plastics in combustible wastes (plastics mix),
Rectangle: fuel oil,
Rhomboid: polyamide,
Triangle: polyethylene and polypropylene
and at the right-hand edge, from top to bottom, a number of biogenic fuels, in GREY:
Rhomboid: cellulose,
Circle: wood,
Rectangle: paper & card,
Bordered rhomboid: typical mix of biogenic materials in combustible wastes (biogenic mix),
Triangle: garden wastes,
Square: kitchen wastes,
in each case with stoichiometric air demand.

The numbers for the chemical composition of plastics mix and biogenic mix, respectively, come from studies carried out in connection with the aforementioned EP 1 715 339: "Method for ascertaining the fractions of biogenic and fossil energy sources" or in accordance therewith.

This direct correlation (conclusion) of $CO_{2_{reference}}$ with the biomass fraction, depicted in FIG. 1, is proposed in particular for a more readily appreciated communication of the results obtained (for the mixing and control of the bunker garbage). For the users of the invention, the operators of garbage incineration plants, it is easier to imagine the temporal variability of the biomass fraction in the garbage input than the fact that the variability of $CO_{2_{reference}}$ already makes a direct statement about the variability of the garbage composition.

Figure 2:
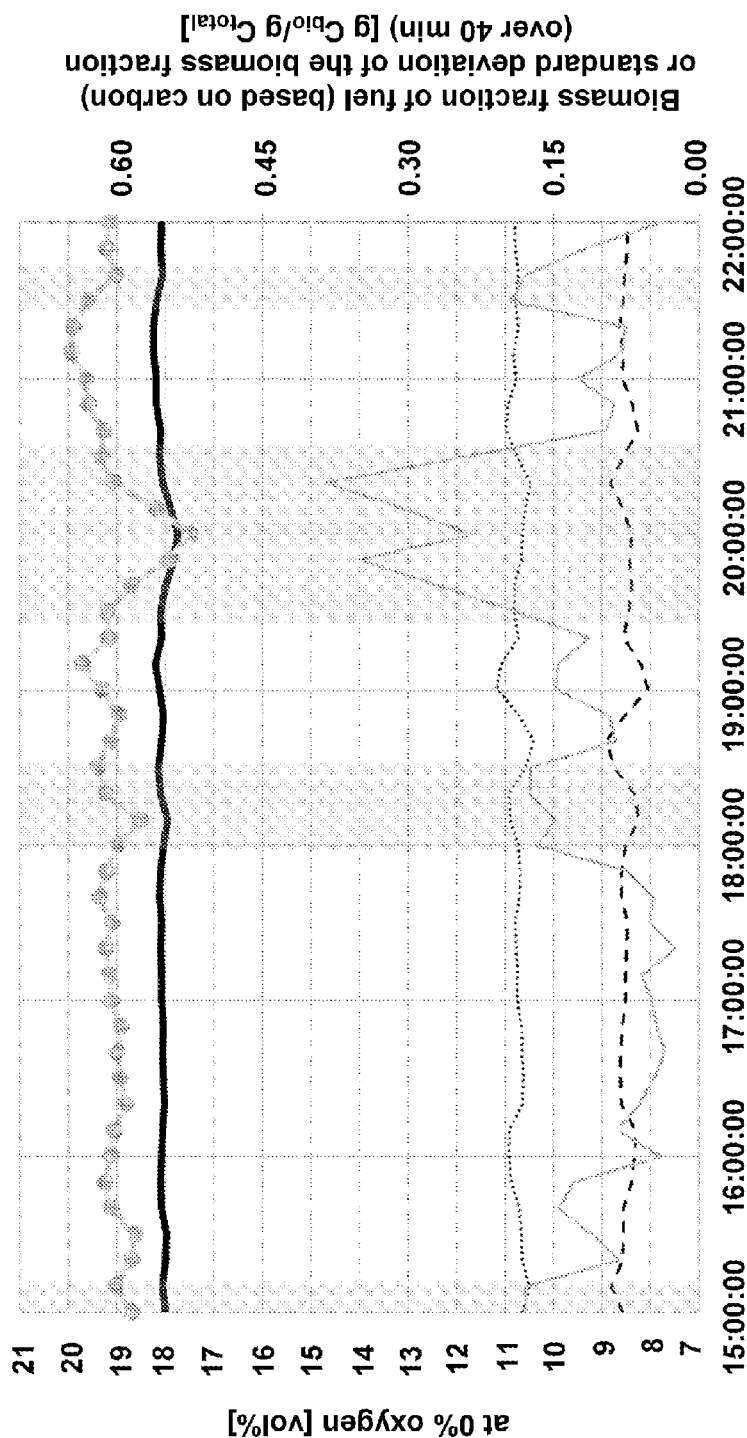
FIG. 2 shows an example of a real-time analysis of the composition of the waste input.

FIG. 2 shows an example of the highly time-resolved analysis of the variability of the composition of the waste input (measured here on the basis of the standard deviation of the biomass fraction) based on carbon, including indication of those periods (regions marked in grey) in which the variability exceeds a specified measure (in this case, the standard deviation of the biomass fraction over 40 min of 0.015 g $C_{bio}$/$C_{total}$) and operation is therefore outside the optimum range for the plant in question.

In these cases, a more intense or more targeted mixing of the bunker garbage is required in order to ensure optimum operation (max. energy efficient, max. garbage throughput, and max. steam production by the garbage incineration plant).

Key:
Dashed line: measured $O_2$ concentration in the dry flue gas,
Dotted line: measured $CO_2$ concentration in the dry flue gas,
Black line: calculated $CO_2$ concentration in the dry flue gas for a reference oxygen content of 0 vol %;
Grey line with dot markings: calculated biomass fraction in the fuel (based on carbon) $C_{bio}$/$C_{total}$,
Grey line: calculated standard deviation of the biomass fraction (based on carbon and shown at 10 times actual level).

Figure 3:
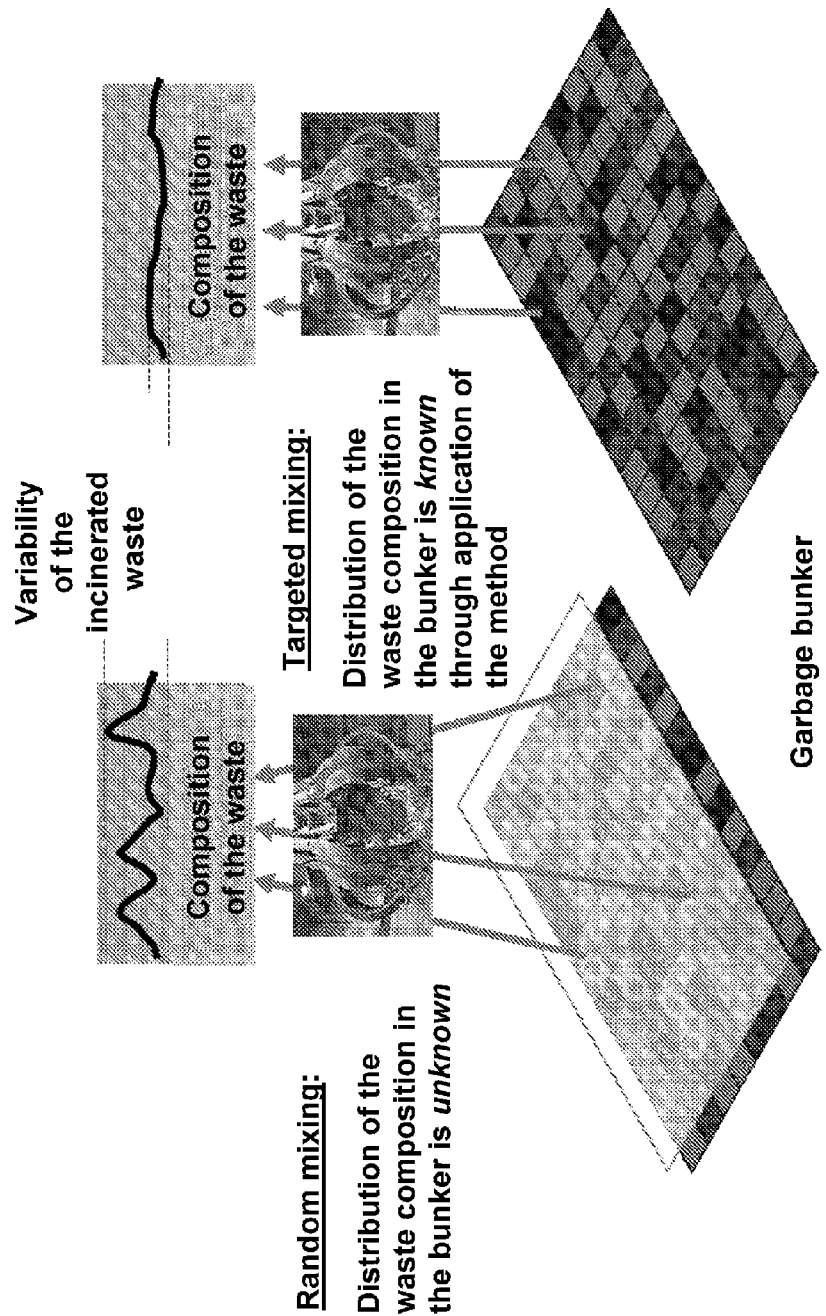
FIG. 3 shows, in two schematic representations, the effect of the mixing optimized according to the invention.

FIG. 3 shows, firstly, the current state of the art in relation to the random mixing of the bunker garbage/fuel feed without knowledge of the spatial distribution of the waste composition in the bunker (left-hand diagram) and, secondly, the targeted and controlled mixing of the bunker garbage/fuel feed, made possible as a result of the present invention, with knowledge of the spatial distribution of the waste composition in the bunker (right-hand diagram); the targeted and controlled mixing leads to less temporal variability in the fuel composition.

FIG. 4 shows, in two representations, an analysis of the short-term variability of the waste composition for 2 garbage incineration plants (plant A and plant B), expressed by the standard deviation of the fraction of biogenic carbon over 4 h [in %] and the respective number of operating hours for which this variability in composition was observed.

Key:
A standard deviation of the fraction of biogenic carbon of <0.5% (column far right) represents very good mixing of the bunker garbage (low temporal variability), whereas a standard deviation of >5% (column far left) points to poor mixing of the bunker garbage (high temporal variability of the waste composition).

FIG. 5 shows, in two representations, for the garbage incineration plant A, in FIG. 5*a* the mean consumption of ancillary fuel in the form of fuel oil and in FIG. 5*b* the mean production of steam as a function of the short-term variability (fluctuations) of the waste composition (expressed by the standard deviation of the fraction of biogenic carbon over 4 h).

Key:

A standard deviation of the fraction of biogenic carbon of <0.5% (column far right) represents very good mixing of the bunker garbage (low temporal variability), whereas a standard deviation of >5% (column far left) points to poor mixing of the bunker garbage (high temporal variability of the waste composition).

Figure 6B:
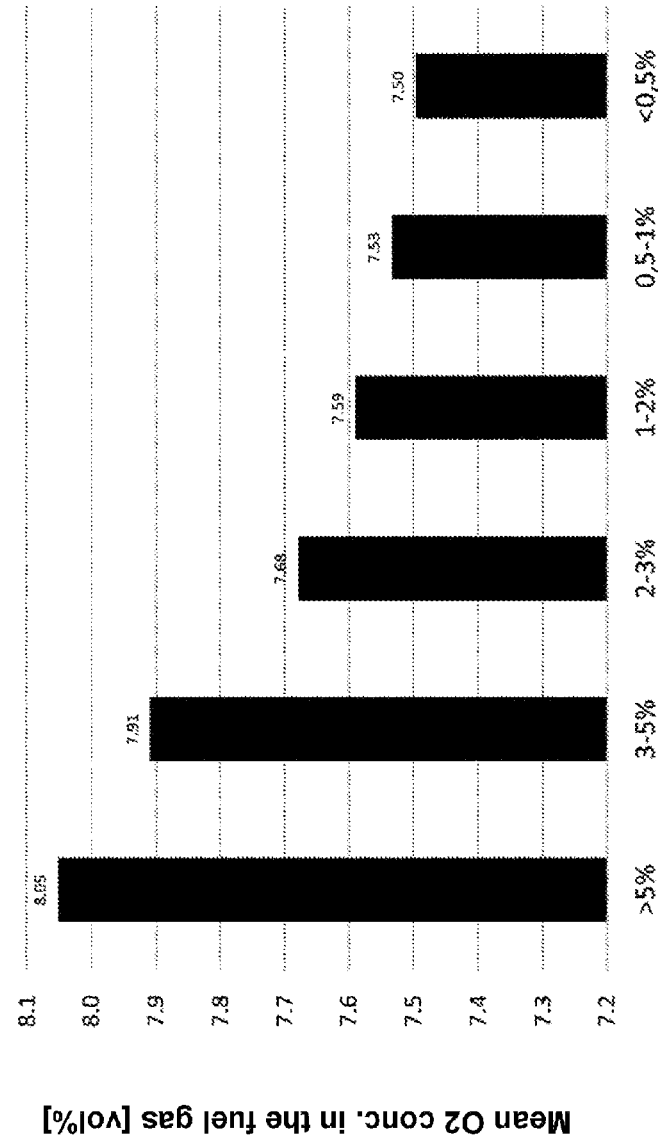

FIG. 6 shows, in two representations, for the garbage incineration plant A, in FIG. 5*a* the mean throughput of waste and in FIG. 6*b* the mean oxygen concentration in the flue gas, again as a function of the short-term variability (fluctuations) of the waste composition (expressed by the standard deviation of the fraction of biogenic carbon over 4 h).

Key:

A standard deviation of the fraction of biogenic carbon of <0.5% (column far right) represents very good mixing of the bunker garbage (low temporal variability), whereas a standard deviation of >5% (column far left) points to poor mixing of the bunker garbage (high temporal variability of the waste composition).

In one embodiment of the invention, for every shovelful fed in (every quantum introduced into the combustion space), the point of its removal in the bunker is detected, this being possible through the control of the frame. After just a time which is characteristic of each plant, that is short overall, the waste composition in the shovelfuls considered affects the composition of the flue gases, and so rapidly there is sufficiently precise knowledge about the composition of the garbage stored in the bunker at the respective sites. As a result of the temporal sequence of the removals and their geometric relationship, this knowledge is continually updated, and rapidly takes account of changes arising from garbage newly introduced into the bunker, as well. In contrast to the prior art, therefore, it is not necessary, when feeding the garbage into the combustion space, to work on the basis of suppositions regarding the bunker garbage composition; instead, a statistically reliable and always up-to-date data stock is available regarding the distribution of the wastes in the bunker and their composition, and can be used not only for fuel charging but also for the mixing of the bunker garbage.

As a result of this measure, success is achieved not only in keeping the fluctuations smaller than in the prior art but also of compensating for them more rapidly than is possible in the prior art.

The following may be stated in summary:

The invention relates to a method for analyzing the operation of garbage incineration plants, which is characterized in that the amount of $CO_2$ in the flue gas is measured and, optionally after return to the quantity $CO_{2_{reference}}$, is employed for determining the ratio of biogenic to fossil carbon in the incinerated garbage, and the variability of $CO_{2_{reference}}$ or of the ratio of biogenic to fossil carbon in the incinerated garbage is determined and recorded by quantity and duration.

The invention further relates to a method for optimizing the operation of garbage incineration plants, characterized in that the amount of $CO_2$ in the flue gas is measured and, optionally after return to the quantity $CO_{2_{reference}}$, is employed for determining the ratio of biogenic to fossil carbon in the incinerated garbage, and the variability of $CO_{2_{reference}}$ or of the ratio of biogenic to fossil carbon in the incinerated garbage is determined by quantity and duration and employed for selecting the garbage to be supplied to the incineration.

The invention also relates to a method for optimizing the operation of garbage incineration plants, characterized in that the amount of $CO_2$ in the flue gas is measured and, optionally after return to the quantity $CO_{2_{reference}}$, is employed for determining the ratio of biogenic to fossil carbon in the incinerated garbage, and the variability of $CO_{2_{reference}}$ or of the ratio of biogenic to fossil carbon in the incinerated garbage is determined by quantity and duration and employed for mixing the garbage stored in the reception bunker.

An (arbitrary) combination of these stated methods is of course possible.

In one embodiment of these, optionally combined, methods, a) in a preparation phase the time from introduction of a quantum of garbage into the combustion space to detection in the flue gas is determined, b) in operation the location of withdrawal of each quantum in the bunker is determined and stored, c) the effect of each quantum on the flue gas, and hence the ratio of biogenic to fossil fuel at this bunker location, is determined with regard to the time determined in step a), and d) with regard to the in preceding steps b) and c) the bunker location for the next withdrawal of a quantum is selected.

e) with regard to the in preceding steps b) and c) the bunker locations for the mixing of the garbage (a quantum is picked up at one location and dispersed at another location in the bunker) is selected.

In one development, when new garbage is introduced into the bunker, the location of the introduction is determined and stored, and up to the first withdrawal of a quantum from this location, the ratio of biogenic to fossil carbon at this bunker location is stored as unknown.

In the description and the claims, "substantially" denotes a deviation of up to 10% of the specified value, if particularly possible, both downwardly and upwardly, otherwise only in the meaningful direction; indications of degrees (angle and temperature) are therefore ±10°.

All amounts data and fractions data, especially those for the purpose of delimiting the invention, unless they relate to the specific examples, should be construed with a tolerance of ±10%; accordingly, for example, 11% means from 9.9% to 12.1%. In the case of designations such as "a/an/one solvent", the word "a/an/one" should be regarded not as a number word but rather as the indefinite article or as a pronoun, unless something else is evident from the context.

Unless otherwise indicated, the term "combination" or "combinations" stands for all types of combinations, starting from two of the relevant constituents up to a multiplicity or all of such constituents; the term "containing" also stands for "consisting of".

The features and variants indicated in the individual embodiments and examples may be used in free combination with those of the other examples and embodiments and particularly for characterizing the invention in the claims without necessarily including the other details of the respective embodiment or respective example.

The invention claimed is:

1. A method for analyzing operation of a garbage incineration plant, comprising the steps of:

measuring an amount of $CO_2$ in flue gas and optionally calculating a $CO_{2reference}$ by normalizing the measured amount to a constant oxygen content; determining a ratio of biogenic to fossil carbon in incinerated garbage using the measured amount of $CO_2$ or the normalized quantity $CO_{2reference}$;

determining and recording a variability of $CO_{2reference}$ or of the ratio of biogenic to fossil carbon in the incinerated garbage by quantity and duration; and selecting garbage to be supplied to the incineration based on the determined and recorded variability of $CO_{2reference}$ or of the ratio of biogenic to fossil carbon in the incinerated garbage by quantity and duration.

2. A method for analyzing operation of a garbage incineration plant, comprising the steps of:

measuring an amount of $CO_2$ in flue gas and optionally calculating a $CO_{2reference}$ by normalizing the measured amount to a constant oxygen content; determining a ratio of biogenic to fossil carbon in incinerated garbage using the measured amount of $CO_2$ or the normalized quantity $CO_{2reference}$;

determining and recording a variability of $CO_{2reference}$ or of the ratio of biogenic to fossil carbon in the incinerated garbage by quantity and duration; and mixing garbage stored in a reception bunker based on the determined and recorded variability of $CO_{2reference}$ or of the ratio of biogenic to fossil carbon in the incinerated garbage by quantity and duration.

3. The method of claim 1, including a) in a preparation phase, determining a time from introduction of a quantum of garbage into a combustion space to detection in the flue gas, b) in operation, determining and storing a location of withdrawal of each quantum in a bunker, c) determining and storing the $CO_{2reference}$ or the ratio of biogenic to fossil carbon at the bunker location through effect of the quantum on the flue gas with regard to the time determined in step a), d) with regard to preceding steps b) and c), selecting a bunker location for a next withdrawal of a quantum selected, and e) with regard to preceding steps b) and c), selecting bunker locations for mixing of the garbage.

4. The method of claim 3, including determining and storing a location of an introduction of new garbage into the bunker upon introduction of the new garbage, wherein, before a first withdrawal of a quantum from this location, the $CO_{2reference}$ or the ratio of biogenic to fossil carbon at this bunker location is stored as unknown, and after the first withdrawal of a quantum from this location the ratio determined according to step c) is stored.

5. The method of claim 2, wherein a) in a preparation phase, determining a time from introduction of a quantum of garbage into a combustion space to detection in the flue gas, b) in operation, determining and storing a location of withdrawal of each quantum in the bunker, c) determining and storing the $CO_{2reference}$ or the ratio of biogenic to fossil carbon at the bunker location through effect of the quantum on the flue gas with regard to the time determined in step a), d) with regard to preceding steps b) and c), selecting a bunker location for a next withdrawal of a quantum selected, and e) with regard to preceding steps b) and c), selecting bunker locations for mixing of the garbage.

6. The method of claim 5, including determining and storing a location of an introduction of new garbage into the bunker upon introduction of the new garbage, wherein, before a first withdrawal of a quantum from this location, the $CO_{2reference}$ or the ratio of biogenic to fossil carbon at this bunker location is stored as unknown, and after the first withdrawal of a quantum from this location the ratio determined according to step c) is stored.

* * * * *